US012578336B2

(12) United States Patent
Mondal et al.

(10) Patent No.: US 12,578,336 B2
(45) Date of Patent: Mar. 17, 2026

(54) ATP DETECTION

(71) Applicant: Promega Corporation, Madison, WI (US)

(72) Inventors: Subhanjan Mondal, Madison, WI (US); Dongping Ma, Madison, WI (US); Kevin Hsiao, Madison, WI (US); Said Goueli, Madison, WI (US); James J. Cali, Madison, WI (US)

(73) Assignee: Promega Corporation, Madison, WI (US)

( * ) Notice: Subject to any disclaimer, the term of this patent is extended or adjusted under 35 U.S.C. 154(b) by 389 days.

(21) Appl. No.: 18/296,785

(22) Filed: Apr. 6, 2023

(65) Prior Publication Data

US 2023/0324390 A1      Oct. 12, 2023

Related U.S. Application Data

(60) Provisional application No. 63/328,070, filed on Apr. 6, 2022.

(51) Int. Cl.
| | |
|---|---|
| *G01N 33/573* | (2006.01) |
| *C12Q 1/66* | (2006.01) |
| *G01N 1/02* | (2006.01) |
| *G01N 21/76* | (2006.01) |

(52) U.S. Cl.
CPC ........... *G01N 33/5735* (2013.01); *C12Q 1/66* (2013.01); *G01N 1/02* (2013.01); *G01N 21/763* (2013.01); *G01N 2001/028* (2013.01)

(58) Field of Classification Search
CPC .. G01N 33/5735; G01N 21/763; G01N 33/50; C12Q 1/66
See application file for complete search history.

(56) References Cited

U.S. PATENT DOCUMENTS

| | | |
|---|---|---|
| 8,603,767 B2 | 12/2013 | Hawkins et al. |
| 2006/0234323 A1 | 10/2006 | Cali et al. |
| 2013/0189717 A1 | 7/2013 | Bugler et al. |

FOREIGN PATENT DOCUMENTS

| | | |
|---|---|---|
| EP | 3215630 B1 | 2/2020 |

OTHER PUBLICATIONS

International Search Report and Written Opinion for PCT/US2023/017740. Mailed Jul. 21, 2023. 16 pages.
Abushaban et al., A new method of assessing bacterial growth in seawater reverse osmosis systems: method development and applications. Conference: The International Desalination Association World CongressAt: São Paulo, BrazilVolume: IDA17WC-58031. Oct. 2017. 13 pages.
Abushaban et al., Assessing Pretreatment Effectiveness for Particulate, Organic and Biological Fouling in a Full-Scale SWRO Desalination Plant. Membranes (Basel). Feb. 27, 2021;11(3):167. 15 pages.
Abushaban et al., ATP measurement in seawater reverse osmosis systems: Eliminating seawater matrix effects using a filtration-based method. Desalination, Mar. 2019, 453(0011-9164):1-9.
Abushaban et al., Direct measurement of ATP in seawater and application of ATP to monitor bacterial growth potential in SWRO pre-treatment systems. Desalination and Water Treatment. Dec. 2017, 99, 91-101.
Abushaban et al., Monitoring Biofouling Potential Using ATP-Based Bacterial Growth Potential in SWRO Pre-Treatment of a Full-Scale Plant. Membranes (Basel). Nov. 21, 2020;10(11):360. 15 pages.
Berkachy et al., Characterisation of the secreted apyrase family of Heligmosomoides polygyrus. Int J Parasitol. Jan. 2021;51(1):39-48.
Branchini et al., Naphthyl- and quinolylluciferin: green and red light emitting firefly luciferin analogues. Photochem Photobiol. May 1989;49(5):689-95.
GenBank PPU31240.1. Photuris pennsylvanica luciferase mRNA, complete cds. Jun. 11, 1997. 2 pages.
GenBank: AAD09177.1. apyrase [Cimex lectularius]. Jun. 5, 2017. 2 pages.
GenBank: AAG17637.1. salivary apyrase [Phlebotomus papatasi] Oct. 2, 2000. 1 page.
Lestinova et al., Insights into the sand fly saliva: Blood-feeding and immune interactions between sand flies, hosts, and Leishmania. PLoS Negl Trop Dis. Jul. 13, 2017;11(7):e0005600. 26 pages.
Manque et al., Identification and Characterization of a Novel Calcium-Activated Apyrase from Cryptosporidium Parasites and Its Potential Role in Pathogenesis. PLoS One, 2012; 7(2): e31030. 11 pages.
NCBI Reference Sequences: NP_001303629. apyrase precursor [Cimex lectularius] Apr. 4, 2024. 2 pages.
NCBI Reference Sequences: NP_006199.2 ectonucleotide pyrophosphatase/phosphodiesterase family member 1 [*Homo sapiens*] Apr. 4, 2024. 5 pages.
NCBI Reference Sequences: XP_024081705. apyrase isoform X1 [Cimex lectularius] Feb. 28, 2018. 2 pages.
Pavankumar et al., Bioanalytical advantages of a novel recombinant apyrase enzyme in ATP-based bioluminescence methods. Anal Chim Acta. Sep. 26, 2018:1025:118-123.
Thore et al., Detection of bacteriuria by luciferase assay of adenosine triphosphate. J Clin Microbiol. Jan. 1975;1(1):1-8.
Valenzuela et al., Purification, cloning, and expression of an apyrase from the bed bug Cimex lectularius. A new type of nucleotide-binding enzyme. J Biol Chem. Nov. 13, 1998;273(46):30583-90.
Valenzuela et al., The salivary apyrase of the blood-sucking sand fly Phlebotomus papatasi belongs to the novel Cimex family of apyrases. J Exp Biol. Jan. 2001;204(Pt 2):229-37.
Volfova et al., The salivary hyaluronidase and apyrase of the sand fly Sergentomyia schwetzi (Diptera, Psychodidae). Insect Biochem Mol Biol. Nov. 2018: 102:67-74.

*Primary Examiner* — Lynn Y Fan
(74) *Attorney, Agent, or Firm* — David W. Staple; Casimir Jones, S.C.

(57) ABSTRACT

The present disclosure relates to devices, methods, and systems or kits for detecting ATP in a sample. Particularly, the present disclosure relates to methods for removing ATP contamination from a sample and detecting intracellular ATP in the sample (e.g., as a proxy for detecting live cells in the sample).

9 Claims, 13 Drawing Sheets

Apyrase treatment
→ No apyrase control
→ 10 seconds
→ 20 seconds
→ 30 seconds
→ 60 seconds Luminescence (RLU)

12,000,000

10,000,000

8,000,000

6,000,000

4,000,000

2,000,000

0

0        50        100        150        200        250

Time in GloMax 20/20 (second)

ATP DETECTION

CROSS-REFERENCE TO RELATED APPLICATIONS

This application claims the benefit of U.S. Provisional Application No. 63/328,070, filed Apr. 6, 2022, the content of which is herein incorporated by reference in its entirety.

FIELD

The present disclosure relates to detecting Adenosine Triphosphate (ATP) in a sample. In particular the disclosure relates to devices, methods, and systems or kits for detecting intracellular ATP in a sample, for example as a determination of live cells in the sample.

BACKGROUND OF THE INVENTION

Millimolar intracellular ATP concentrations are a relatively constant feature of all living cells, and this ATP is rapidly degraded upon cell death. Therefore, the measurement of intracellular ATP is performed as a means of detecting and quantifying the presence of living cells such as pathogenic and non-pathogenic bacteria. Traditional approaches for ATP detection require outgrowth of contaminating cells in or on a nutrient medium and can take up to several days and cannot detect viable but unculturable cells. False positive signals due to the presence of free ATP are also frequently encountered. Current methods for minimizing or eliminating free-ATP-dependent false positives by ATPase treatment are not directly compatible with subsequent live-cell ATP measurements.

SUMMARY OF THE INVENTION

Disclosed herein are methods comprising fully or partially removing ATP contamination from a sample. In some embodiments, the methods comprise incubating the sample with a conditionally active ATP-degrading enzyme selected from the group consisting of: *Cimex lectularius* apyrase, *Phlebotomus papatasi* apyrase, ectonucleotide pyrophosphatase/phosphodiesterase 1 (ENPP1), and combinations thereof.

In some embodiments, the sample is incubated for less than about five minutes (e.g., less than 4 minutes, less than 3 minutes, less than 2 minutes, or less than 1 minute). In some embodiments, the sample is incubated for about 5 to about 60 seconds.

In some embodiments, the methods further comprise conducting a biological assay with a sample obtained following the incubating. In some embodiments, the biological assay comprises detecting ATP remaining in the sample obtained following the incubating. In some embodiments, detecting the ATP remaining in the sample comprises a bioluminescent assay. In some embodiments, the presence of ATP indicates presence of live cells in the sample.

In some embodiments, the methods further comprise inhibiting the conditionally active ATP-degrading enzyme in a sample obtained following the incubating. In some embodiments, the inhibiting comprises contacting the sample with EGTA, a zinc chelator, a small molecule inhibitor, or a combination thereof.

In some embodiments, the methods further comprise lysing cells in a sample obtained following the incubating and/or prior to conducting the biological assay.

Further disclosed herein a methods of detecting intracellular ATP. The methods may comprise at least one or all of: collecting a sample comprising or suspected of comprising cells; incubating the sample with a conditionally active ATP-degrading enzyme to substantially degrade any extracellular ATP in the sample; inhibiting the conditionally active ATP-degrading enzyme; lysing the cells; and determining the presence or amount of ATP. In some embodiments, the conditionally active ATP-degrading enzyme is selected from the group consisting of: *Cimex lectularius* apyrase, *Phlebotomus papatasi* apyrase, ectonucleotide pyrophosphatase/phosphodiesterase 1 (ENPP1), and combinations thereof.

In some embodiments, the sample comprises or is suspected of comprising a microorganism. In some embodiments, the sample is collected on an absorbent pad. In some embodiments, the absorbent pad is prewetted with a solution containing the conditionally active ATP-degrading enzyme. In some embodiments, the sample is a liquid sample. In some embodiments, the sample is an environmental sample.

In some embodiments, inhibiting comprises contacting the sample with EGTA, a zinc chelator, a small molecule inhibitor, or a combination thereof.

In some embodiments, determining the presence or amount of ATP comprises a bioluminescent assay. In some embodiments, the ATP detection reagent comprises a luciferase enzyme and a luciferin substrate.

In some embodiments, the sample is incubated for less than about five minutes (e.g., less than 4 minutes, less than 3 minutes, less than 2 minutes, or less than 1 minute). In some embodiments, the sample is incubated for about 5 to about 60 seconds.

In some embodiments, the method is performed in less than about 10 minutes (e.g., less than 9 minutes, less than 8 minutes, less than 7 minutes, less than 6 minutes, less than 5 minutes, less than 4 minutes, less than 3 minutes, less than 2 minutes, or less than 1 minute).

Also disclosed herein are assay devices. The assay devices may comprise at least one or all of: a swab assembly comprising a collection swab configured to receive and absorb a sample, and a cap comprising a reservoir comprising reaction buffer; and a reaction chamber configured to receive the swab assembly. In some embodiments, the collection swab is prewetted with a solution comprising a conditionally active ATP-degrading enzyme. In some embodiments; the conditionally active ATP-degrading enzyme is selected from the group consisting of: *Cimex lectularius* apyrase, *Phlebotomus papatasi* apyrase, ectonucleotide pyrophosphatase/phosphodiesterase 1 (ENPP1), and combinations thereof.

In some embodiments, the reservoir comprises an articulable element to release the reaction buffer into the reaction chamber. In some embodiments, the reaction buffer comprises a cell lysis reagent, an inhibitor of the conditionally active ATP-degrading enzyme, an ATP detection reagent, or a combination thereof.

In some embodiments, the inhibitor of the conditionally active ATP-degrading enzyme comprises EGTA, a zinc chelator, a small molecule inhibitor, or a combination thereof.

In some embodiments, the solution comprising a conditionally active ATP-degrading enzyme further comprises a divalent cation.

Additionally disclosed are methods of detecting intracellular ATP using the disclosed assay devices. In some embodiments, the methods comprise at least one or all of: collecting the sample on the collection swab of a disclosed assay device; placing the swab assembly in the reaction chamber; deploying the reaction buffer from the cap; and determining the presence or amount of intracellular ATP in the sample.

In some embodiments, the method is performed in less than about 10 minutes (e.g., less than 9 minutes, less than 8 minutes, less than 7 minutes, less than 6 minutes, less than 5 minutes, less than 4 minutes, less than 3 minutes, less than 2 minutes, or less than 1 minute).

In some embodiments, the sample is a liquid sample. In some embodiments, the sample is an environmental sample.

In some embodiments, determining the presence or amount of ATP comprises a bioluminescent assay. In some embodiments, the ATP detection reagent comprises a luciferase enzyme and a luciferin substrate.

Disclosed herein are kits comprising at least one or all of: a conditionally active ATP-degrading enzyme; a swab assembly comprising: a collection swab configured to receive and absorb a sample and a cap; a reaction chamber configured to receive the swab assembly; and a reaction buffer comprising a cell lysis reagent, an inhibitor of the conditionally active ATP-degrading enzyme, an ATP detection reagent, or a combination thereof.

In some embodiments, the conditionally active ATP-degrading enzyme is on the collection swab.

In some embodiments, the reaction buffer is in a reservoir in the cap.

In some embodiments, the conditionally active ATP-degrading enzyme is selected from the group consisting of: *Cimex lectularius* apyrase, *Phlebotomus papatasi* apyrase, ectonucleotide pyrophosphatase/phosphodiesterase 1 (ENPP1), and combinations thereof.

Other aspects and embodiments of the disclosure will be apparent in light of the following detailed description and accompanying figures.

BRIEF DESCRIPTIONS OF THE DRAWINGS

Figure 1:
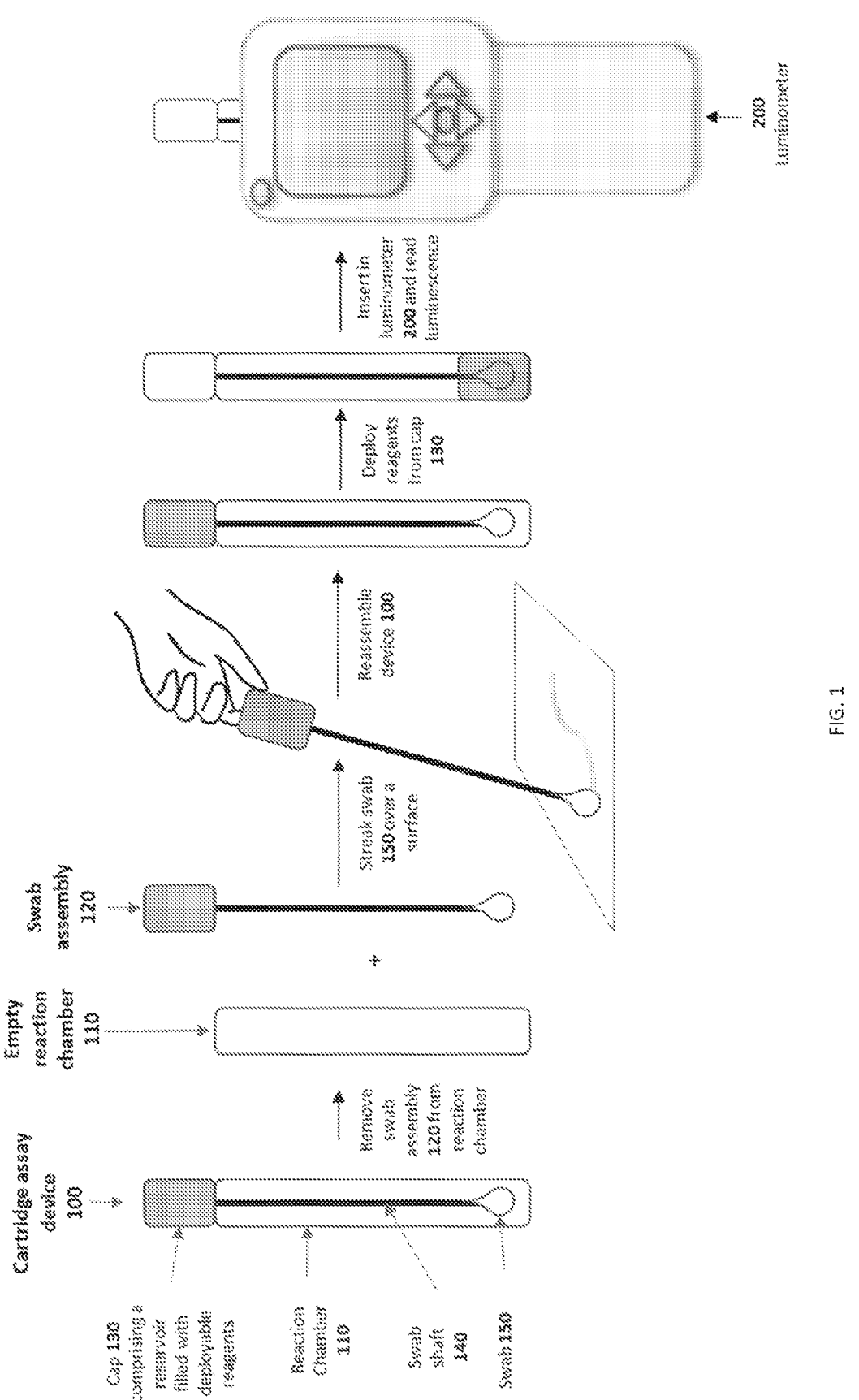
FIG. 1 is a schematic of the system and workflow for ATP detection utilizing an exemplary sample collection and assay device cartridge.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION OF THE INVENTION

The present disclosure provides technology related to detection of ATP in a sample. Particularly, the present disclosure provides devices, systems, kits, and methods for sample collection and live cell ATP detection.

Prior devices and formats for detecting surface contamination detect total ATP, which includes free ATP plus the ATP contained in live cells. Free ATP represents a background that can both limit sensitivity for cell detection and present as a false positive signal. A two-cartridge approach for selectively detecting only live cell ATP versus total cellular plus free ATP has been applied to liquid samples. In these cases, substantially identical aliquots of a liquid sample are captured by each of the two cartridges, and the free ATP value is subtracted from total to obtain a live cell only value. This approach is unsustainable for surface testing due to the high unlikelihood of collecting two substantially identical samples. The methods, systems, and devices disclosed herein allow for consolidation of free ATP elimination with live cell ATP detection in a single sample (e.g., a surface swab) and solves the large challenge of providing a matched free ATP control by way of an orthogonal sample.

The disclosed devices and methods also allow for live cell ATP detection with improved sensitivity and selectivity, decreased cost, and a simplified workflow. The improved methods and devices employ conditionally active ATP-degrading enzymes that are cost-efficient in the amount needed for depletion of ATP contamination in a brief amount of time, sensitive to an inhibitor suitable for incorporation in a dual-purpose reagent for cell lysis and luciferase-dependent ATP detection without inhibiting either activity, and stable for storage and formulation in a preloaded swab. As shown, extracellular ATP was substantially depleted in about 5 to about 60 seconds, and the ATP-degrading enzyme was rapidly inhibited to an extent that detection of ATP of interest (e.g., live cell ATP) was selective and sensitive. In an exemplary assay device as described herein, a result may be provided in less than or equal to one minute from sample collection. Previous devices, formats, and/or reagents have mostly used *Solanum tuberosum* (potato) apyrase as an extracellular ATP-eliminator, however, its inactivation requires measures, such as high temperature or extreme pH treatment, that are not suitable for use with the sensitivity and selectivity, decreased cost, simplified workflow, and speed of the disclosed methods and devices.

1. DEFINITIONS

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and," and "the" include plural references unless the context clearly dictates otherwise. The present disclosure also contemplates other embodiments "comprising," "consisting of," and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

As used herein, the term "bioluminescence" refers to production and emission of light by a chemical reaction catalyzed by, or enabled by, an enzyme, protein, protein complex, or other biomolecule (e.g., bioluminescent complex). In typical embodiments, a substrate for a bioluminescent entity (e.g., bioluminescent protein or bioluminescent complex) is converted into an unstable form by the bioluminescent entity the substrate subsequently emits light.

As used herein, the term "reagent" refers to a composition, e.g., comprising a chemical (e.g., organic compounds and inorganic compounds), enzymes, and combinations thereof. A reagent can be provided in gaseous, solid, or liquid form, or any combination thereof, and can be a component of a solution or suspension. In some embodiments, a reagent includes fluids useful in methods of detecting ATP in a sample, such as cell lysis buffers, bioluminescent reagents, ATP eliminating enzyme inactivating agents, buffers, and the like.

As used herein, the term "detection" refers to the qualitative determination of the presence or absence of an analyte in a sample. The term "detection" further includes the quantification of an analyte in a sample, e.g., the amount and/or concentration of an analyte in a sample. The term "detection" also includes the "identification" of an analyte. As used herein, the word "presence" or "absence" (or, alternatively, "present or "absent") is used in a relative sense to describe the amount or level of a particular entity (e.g., an analyte, e.g., ATP). For example, when an analyte is said to be "present" in a test sample, it means the level or amount of this analyte is above a pre-determined threshold; conversely, when an analyte is said to be "absent" in a test sample, it means the level or amount of this analyte is below a pre-determined threshold. The pre-determined threshold may be the threshold for detectability associated with the particular test used to detect the analyte or any other threshold. When an analyte is "detected" in a sample it is "present" in the sample; when an analyte is "not detected" it is "absent" from the sample. Further, a sample in which an analyte is "detected" or in which the analyte is "present" is a sample that is "positive" for the analyte. A sample in which an analyte is "not detected" or in which the analyte is "absent" is a sample that is "negative" for the analyte.

The term "contacting" as used herein refers to bring or put in contact, to be in or come into contact. The term "contact" as used herein refers to a state or condition of touching or of immediate or local proximity.

"Variant" is used herein to describe a peptide or polypeptide that differs in amino acid sequence by the insertion, deletion, or conservative substitution of amino acids, but retain at least one biological activity. Variant is also used herein to describe a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree, and distribution of charged regions) is recognized in the art as typically involving a minor change. "Variant" also can be used to describe a polypeptide or a fragment thereof that has been differentially processed, such as by proteolysis, phosphorylation, or other post-translational modification, yet retains its biological activity.

As used herein, the term "sample" is used in its broadest sense. In one sense, it is meant to include a specimen obtained from any source, including biological and environmental samples. In another sense, it refers to any sample comprising or suspected of comprising ATP. Biological samples may be obtained from animals (including humans) and encompass fluids, solids, tissues, and gases. Such examples are not however to be construed as limiting the sample types. In some embodiments, the sample is a fluid sample such as a liquid sample. Examples of liquid samples include bodily fluids (e.g., blood, serum, plasma, saliva, urine, ocular fluid, semen; sputum, sweat, tears, and spinal fluid), water samples (e.g., samples of water from oceans, seas, lakes, rivers, and the like), samples from home, municipal, or industrial water sources, runoff water, or sewage samples; and food samples (e.g.; milk, beer, juice, or wine). Viscous liquid, semisolid, or solid specimens may be used to create liquid solutions, eluates, suspensions, or extracts that can be samples. Liquid samples can be made from solid, semisolid, or highly viscous materials, such as soils, fecal matter, tissues, organs, biological fluids, or other samples that are not fluid in nature. For example, solid or semisolid samples can be mixed with an appropriate solution, such as a buffer, a diluent, and/or extraction buffer. The sample can be macerated, frozen and thawed, or otherwise extracted to form a fluid sample. In some embodiments, the sample is a wipe from environmental surfaces. In environmental or other non-clinical applications, the sample may be derived from soils, dust, vegetation, or food, or environmental swabs (e.g., food and beverage production/preparation environments, clinical hygiene testing environments, and the like).

Samples can comprise biological materials, such as cells, microbes, organelles, and biochemical complexes. In some embodiments, the sample is suspected of containing a microorganism. Nonlimiting examples of suitable samples suspected of containing a microorganism include environmental samples (e.g., surface swabs/sponges, soil, sediments, fomites), food (e.g., raw materials, in-process samples, and finished-product samples), beverages, clinical/veterinary samples (e.g., blood, serum, plasma, urine, sputum, tissue, mucous, feces, wound exudate, pus, cerebrospinal fluid), and water (e.g., surface water, potable water, process water). In some embodiments, the samples include food-handling surface samples (e.g., conveyor belts, blades, cutting surfaces, mixing equipment surfaces, filters, storage containers), room samples (e.g., walls, floors, drains, ventilation equipment), and cleaning equipment (e.g., hoses, cleaning tools). The microorganism can be indicative of a specific contamination, or an indicator of general sanitation.

Unless otherwise defined herein, scientific and technical terms used in connection with the present disclosure shall have the meanings that are commonly understood by those of ordinary skill in the art. The meaning and scope of the terms should be clear; in the event, however of any latent ambiguity, definitions provided herein take precedent over any dictionary or extrinsic definition. Further, unless otherwise required by context, singular terms shall include plu-
ralities and plural terms shall include the singular.

Preferred methods and materials are described below,
although methods and materials similar or equivalent to
those described herein can be used in practice or testing of
the present disclosure. All publications, patent applications,
patents and other references mentioned herein are incorpo-
rated by reference in their entirety. The materials, methods,
and examples disclosed herein are illustrative only and not
intended to be limiting.

2. METHODS

The disclosure provides methods comprising fully or
partially removing ATP contamination from a sample by
incubating the sample with a conditionally active ATP-
degrading enzyme. In some embodiments, the ATP-degrad-
ing enzyme may be selected from the group consisting of:
*Cimex lectularius* apyrase (for example, NCBI Reference
Sequences: NP_001303629 and XP_024081705 and Gen-
Bank: AAD09177.1), *Phlebotomus papatasi* apyrase (for
example, GenBank: AAG17637.1), ectonucleotide pyro-
phosphatase/phosphodiesterase 1 (ENPP1) (for example,
NCBI Reference Sequence: NP_006199.2), and combina-
tions thereof. In select embodiments, the ATP-degrading
enzyme is *Phlebotomus papatasi* apyrase.

The sample may be incubated with the conditionally
active ATP-degrading enzyme for a period of time necessary
to substantially deplete the sample of ATP contamination.
For example, the incubation may remove more than 50%,
more than 60%, more than 70%, more than 80%, more than
90%, or more of the ATP contamination. Level of depletion
of the sample of ATP contamination can be determined using
the methods described in the Examples herein, particularly
Examples 1 and 2.

In some embodiments, the sample is incubated for less
than about five minutes (e.g., about five minutes, about four
minutes, about three minutes, about two minutes, about one
minute, or less). In some embodiments, the sample is
incubated for about 5 to about 60 seconds (e.g., about five
seconds, about 10 seconds, about 20 seconds, about 30
seconds, about 40 seconds, about 50 seconds, or about 60
seconds).

The incubation is typically carried out at room tempera-
ture, although any temperature necessary to substantially
deplete the sample of ATP contamination is suitable for use
with the disclosed methods.

In some embodiments, incubating the sample with a
conditionally active ATP-degrading enzyme comprises incu-
bating the sample with a solution comprising the condition-
ally active ATP-degrading enzyme and other components,
including for example, buffers, additives, salts, stabilizers,
and the like. In some embodiments, the solution further
comprises divalent cations, e.g., calcium, magnesium, and/
or zinc ions as co-factors for the conditionally active ATP-
degrading enzyme. Preferably, the divalent cations are pro-
vided as salts, e.g., $CaCl_2$, $ZnCl_2$, or $MgCl_2$. Suitable
concentrations of the divalent cation range from 1 to 6 mM.

The particular concentrations and/or amounts of the con-
ditionally active ATP-degrading enzyme will vary depend-
ing on the enzyme used, and the volume and type of sample.
In some embodiments, about 0.1 to about 20 μg of the
conditionally active ATP-degrading enzyme is incubated
with the sample. In some embodiments, about 0.1-15 μg,
about 0.1-10 μg, about 0.1-5 μg, about 0.1-2 μg, about 0.1-1
μg, about 0.5-20 μg, about 0.5-15 μg, about 0.5-10 μg, about
0.5-5 μg, about 0.5-2 μg, about 0.5-1 μg, about 1-20 μg, about 1-15 μg, about 1-10 μg, about 1-5 μg, about 1-2 μg,
about 5-10 μg, about 5-15 μg, about 5-20 μg, about 10-20 μg,
or about 15-20 μg of the conditionally active ATP-degrading
enzyme is incubated with the sample.

The methods may further comprise conducting a biologi-
cal assay with sample obtained following the incubation. In
some embodiments, the biological assay detects the pres-
ence, absence, or quantity of at least one analyte or bio-
marker. The analyte may be a protein, a nucleic acid, an
antigen, a metabolite, or a fragment thereof.

In some embodiments, the biological assay comprises
determining the presence or amount of ATP in the sample
obtained following the incubation with a conditionally
active ATP-degrading enzyme. Detecting or determining the
amount of ATP in the sample may comprise any method
which qualitatively or quantitatively determines the pres-
ence of ATP in the sample.

In some embodiments, detecting ATP comprises a biolu-
minescent assay or an assay with a detectable light product.
In particular, any bioluminescence generating-enzyme that
is ATP-dependent may be suitable for use in the methods of
the present invention. In some embodiments, ATP detection
comprises detecting luminescence generated by a luciferase-
luciferin reaction with a luminometer although other detec-
tion means may be used. The presence of light greater than
background level indicates the presence of ATP in the
sample. Suitable control reactions are readily designed by
one of skill in the art.

In some embodiments, the method further comprises
inhibiting the conditionally active ATP-degrading enzyme
prior to conducting the bioassay and/or after the incubation
with the conditionally active ATP-degrading enzyme. Meth-
ods of inhibiting the conditionally active ATP-degrading
enzyme are dependent upon the choice of conditionally
active ATP-degrading enzyme and downstream applications
of the sample (e.g., biological assay). In some embodiments,
the inhibiting comprises contacting the sample with an
inhibitor of the conditionally active ATP-degrading enzyme,
including for example, any small molecule, ion, protein,
ligand, or the like which effectively stops the enzymatic
reaction with ATP. In some embodiments, the inhibiting
comprises contacting the sample with EGTA, a zinc chela-
tor, a small molecule inhibitor, or a combination thereof. In
some embodiments, the inhibitor of the conditionally active
ATP-degrading enzyme comprises EGTA which is suitable
for inhibiting calcium- and or zinc-dependent ATP-degrad-
ing enzymes, such as any of *Cimex lectularius* apyrase,
*Phlebotomus papatasi* apyrase, and ectonucleotide pyro-
phosphatase/phosphodiesterase 1 (ENPP1). In some
embodiments, the inhibitor of the conditionally active ATP-
degrading enzyme comprises a zinc chelator which is suit-
able for inhibiting zinc-dependent ATP-degrading enzymes,
such as ENPP1. In select embodiments, the zinc chelator
comprises N,N,N',N'-tetrakis(2-pyridinylmethyl)1,2-ethane-
diamine (TPEN). In some embodiments, the inhibitor of the
conditionally active ATP-degrading enzyme comprises the
small molecule inhibitor 6-[(3-aminophenyl)methyl]-N,N,5-
trimethyl-[1,2,4]triazolo[1,5-a]pyrimidin-7-amine, also
known as Inhibitor C, suitable for use in inhibiting ENPP1.

The particular concentrations and/or amounts of the
inhibitor of the conditionally active ATP-degrading enzyme
will depend on the particular conditionally active ATP-
degrading enzyme used. Preferably, at least about five times
the inhibitor's $IC_{50}$ concentration of the particular condi-
tionally active ATP-degrading enzyme is used.

The method may further comprise lysing cells in sample
obtained following the incubation prior to conducting the biological assay. In some embodiments, the cells are lysed by chemical or enzymatic methods, e.g., treatment with detergents, pH modifying agents, or membrane rupturing small molecules or enzymes.

Therefore, the present disclosure further provides methods for detecting intracellular ATP in a sample, for example a sample suspected of containing cells. In some embodiments, methods suitable for detecting intracellular ATP in a sample may comprise collecting a sample suspected of containing cells, incubating the sample with a conditionally active ATP-degrading enzyme, inhibiting the conditionally active ATP-degrading enzyme, lysing the cells, and determining the presence or amount of ATP.

In some embodiments, the sample is collected on an absorbent pad. In some embodiments, the absorbent pad is prewetted with a solution containing the conditionally active ATP-degrading enzyme. Thus, in some embodiments, the incubation with a conditionally active ATP-degrading enzyme is carried out on the absorbent pad.

Since the concentration of ATP is fairly constant in the cell, measurement of ATP content in a sample can be used as a proxy to detect or determine the number of viable cells. Thus, the detection of intracellular ATP in the sample may provide an indication of live cells in the sample (e.g., microbial contamination). As such, the disclosure also provides methods for detecting or determining live cells in a sample (e.g., microbial contamination) of a sample.

In some embodiments, the methods may use the assay devices as described herein. In some embodiments, the methods comprise collecting the sample on the collection swab of the assay device. The swab is first removed from the empty reaction chamber and streaked across a surface or, in the case of a liquid sample, applied directly to the swab tip by dipping, wicking, or placing the liquid sample on the swab with a dropper or pipette. After the swab is inserted or placed into the reaction chamber, the reaction buffer is deployed from the reservoir into the receptacle to contact the swab. Contacting the reagent with the swab results in a luminescent reaction with the luciferase enzyme and its luciferin substrate for determination of the presence or amount of ATP in the sample.

The disclosed methods allow for full or partial removal of ATP contamination and/or ATP detection with improved sensitivity and selectivity in a short amount of time. In some embodiments, the methods are performed in less than about 10 minutes, e.g., 10 seconds to 10 minutes, 10 seconds to 5 minutes, 10 seconds to 2 minutes, 10 seconds to 1 minutes, 30 seconds to 10 minutes, 30 seconds to 5 minutes, 30 seconds to 2 minutes, 30 seconds to 1 minutes, 1-5 minutes, or 1-2 minutes. The methods may be performed in about 1 minute, about 2 minutes, about 3 minutes, about 4 minutes or about 5 minutes.

3. ASSAY DEVICE

The technology relates to assay device 100 (FIG. 1). In some embodiments, the technology relates to analytical devices that are suitable for use in a variety of settings that allow delivery of an analytical result that is rapid with minimum degree of skill and involvement from the user, including but not limited to, food and beverage production/ preparation environments, clinical hygiene testing environments (e.g., surgical equipment and patient exposed materials and surfaces), safety testing for clinical and consumer products, environmental testing application (e.g., water contamination), sterility testing, and the like. As used herein, the term "assay device," "assaying device," and "detection device" are used interchangeably to refer to a device for detecting the presence, absence, concentration, and/or amount of ATP in a sample or specimen.

With reference to FIG. 1, an exemplary assay device 100 is illustrated. Device 100 includes a reaction chamber 110 and a swab assembly 120. In the illustrated embodiment, swab assembly 120 includes cap 130 comprising a reservoir filled with deployable reagents, swab shaft 140, and collection swab 150. The assay device may be of any size or shape. In some embodiments, the size, shape, and orientation are configured for use in or with an optical detection device.

With continued reference to FIG. 1, collection swab 150 comprises an absorbent pad (e.g., a cotton pad) configured to receive and absorb a sample. In some embodiments, collection swab 150 is prewetted with a solution containing a conditionally active ATP-degrading enzyme. The conditionally active ATP-degrading enzyme is selected from the group consisting of: *Cimex lectularius* apyrase, *Phlebotomus papatasi* apyrase, ectonucleotide pyrophosphatase/ phosphodiesterase 1 (ENPP1), and combinations thereof. In some embodiments, the conditionally active ATP-degrading enzyme is *Phlebotomus papatasi* apyrase.

In some embodiments, about 0.1-20 μg, about 0.1-15 μg, about 0.1-10 μg, about 0.1-5 μg, about 0.1-2 μg, about 0.1-1 μg, about 0.5-20 μg, about 0.5-15 μg, about 0.5-10 μg, about 0.5-5 μg, about 0.5-2 μg, about 0.5-1 μg, about 1-20 μg, about 1-10 μg, about 1-5 μg, about 1-2 μg, about 5-10 μg, about 5-15 μg, about 5-20 μg, about 10-20 μg, or about 15-20 μg of the conditionally active ATP-degrading enzyme is prewetted on the collection swab.

The solution containing the conditionally active ATP-degrading enzyme may further comprise buffers, additives, salts, stabilizers, and the like, which do not have a negative downstream effect on the detection of ATP and/or lysis of cells within the sample. In some embodiments, the solution further comprises divalent cations, e.g., calcium, magnesium, and/or zinc ions as co-factors for the conditionally active ATP-degrading enzyme. In some embodiments, the divalent cations are provided as salts, e.g., $CaCl_2$, $ZnCl_2$, or $MgCl_2$. In some embodiments, the solutions comprise 1-6 mM (e.g., about 1 mM, about 3 mM, about 5 mM) of the divalent cation.

The device further comprises cap 130. Cap 130 may comprise a reservoir comprising reaction buffer. In some embodiments, the reservoir comprises an articulable element to release the reaction buffer into the reaction chamber. In some embodiments, the articulable element comprises a seal which can be broken or a valve which may be opened to dispense the reaction buffer into the reaction chamber. Any means for sequestering the reaction buffer in the reservoir which allows a user to release the reaction buffer into the reaction chamber is suitable for use with the device.

The reaction buffer may comprise a cell lysis reagent, an inhibitor of the conditionally active ATP-degrading enzyme, an ATP detection reagent, or a combination thereof.

Lysis reagents (e.g., a lysis reagent in a lysis buffer) are known to one of skill in the art. In some embodiments, the cell lysis reagent comprises a detergent, such as a mild non-denaturing detergent (e.g., Triton® X-100 or CHAPS), or other detergents with lytic activity against microorganisms. In some embodiments, the cell lysis reagent comprises enzyme(s) or other agent(s) that promote the lysis, including for example, lysozyme, labiase, lysostaphin, achromopeptidase, alpha-homolysin, chitinase, streptolysin O, tetanolysin, and mutanolysin.

The inhibitor of the conditionally active ATP-degrading enzyme may include one or more small molecule, ion, protein, ligand, or the like which effectively stops the enzymatic reaction with ATP. In some embodiments, the inhibitor of the conditionally active ATP-degrading enzyme comprises EGTA. In some embodiments, the inhibitor of the conditionally active ATP-degrading enzyme comprises a zinc chelator. In select embodiments, the zinc chelator comprises N,N,N',N'-tetrakis(2-pyridinylmethyl)-1,2-ethanediamine (TPEN). In some embodiments, the inhibitor of the conditionally active ATP-degrading enzyme comprises a small molecule inhibitor. In select embodiment, the small molecule inhibitor comprises 6-[(3-aminophenyl)methyl]-N,N,5-trimethyl-[1,2,4]triazolo[1,5-a]pyrimidin-7-amine, also known as Inhibitor C. In some embodiments, the inhibitor of the conditionally active ATP-degrading enzyme comprises two or more of any of EGTA, a zinc chelator, and a small molecule inhibitor.

The ATP detection reagent may comprise any reagent useful in measuring ATP presence in a qualitative or quantitative manner, including for example, products that provide a detectable light product. In particular, any bioluminescence generating-enzyme that is ATP-dependent may be suitable for use in the methods and devices of the present invention.

In some embodiments, the ATP detection reagent comprises a luciferase enzyme and a luciferin substrate. The luminescence generated by a luciferase-luciferin reaction is typically detected with a luminometer although other detection means may be used. The presence of light levels greater than background level indicates the presence of ATP, and thus, in some embodiments, live cells, in the sample. Suitable control reactions are readily designed by one of skill in the art.

The materials needed, and the particular concentrations and/or amounts, of the materials needed to generate a luminescent signal will vary depending on the luciferase enzyme being used. In some embodiments, the ATP detection reagent further comprises co-factors and other molecules useful for the reaction. In general, for beetle luciferases, the additional materials can include a magnesium ($Mg^{2+}$) salt such as magnesium sulfate. In some embodiments, other materials can be added to the solution including: a buffer to maintain the reaction at the proper pH, an additive such as PRIONEX or Bovine serum albumin (BSA) to help maintain luciferase activity, reducing agents, detergents, esterases, salts, amino acids (e.g., D-cysteine), etc.

The term "luciferin substrate" as used herein refers to a molecule capable of creating light via a chemical or biochemical reaction (e.g., luciferin, luciferin derivative, or a functional analog thereof) The luciferin substrate may be a molecule capable of creating light generated by a luciferase. Suitable luciferin substrates for luciferase enzymes include luciferin, luciferin derivatives, and functional analogs of luciferins. The naturally-occurring substrate for beetle luciferases is firefly luciferin, a polytherocyclic organic acid, D-(−)-2-(6'-hydroxy-2'-benzoth-iazolyl)-Δ2-thiazolin-4-carboxylic acid (D-luciferin). Luciferin may be isolated from nature (e.g., from fireflies) or synthesized. Synthetic luciferin can have the same structure as the naturally occurring luciferin or can be derivatized, so long as it functions analogously. Examples of derivatives of luciferin include D-luciferin methyl ester and other esters of luciferin that are hydrolyzed or acted upon by esterases in a sample to yield luciferin, and naphthyl- and quinolyl-luciferin (Branchini et al., 1989). There are multiple commercial sources for luciferin (e.g., Promega Corp. Madison, Wis.).

Any luciferase enzyme or variant or derivative thereof that meets the limitations set forth herein, e.g., luciferases that use ATP as substrate, may be used in the methods, devices or kits disclosed herein. To date, several classes of luciferases have been identified. Of these, beetle luciferases, such as that of the common firefly (family Lampyridae), form a distinct class with unique evolutionary origins. Suitable luciferase enzymes include, but are not limited to, those selected from the group consisting of: *Photinus pyralis* or North American firefly luciferase; *Luciola cruciata* or Japanese firefly or Genji-botaru luciferase; *Luciola italic* or Italian firefly luciferase; *Luciola lateralis* or Japanese firefly or Heike luciferase; *Luciola mingrelica* or East European firefly luciferase; *Photuris pennsylvanica* or Pennsylvania firefly luciferase; *Pyrophorus plagiophthalamus* or Click beetle luciferase; and *Phrixothrix hirtus* or Railroad worm luciferase. Optionally, the luciferases used in the compositions and methods of the invention have enhanced thermo-stability and/or chernostability properties.

In some embodiments, *Photuris pennsylvanica* firefly luciferase (LucPpe2; 545 amino acid residues; GenBank 2190534), or derivative or variant thereof is used. Thermo-stable and/or chemostable mutant luciferases derived from LucPpe2 (e.g., LucPpe2m78 (also known as 78-0B10); LucPpe2m90 (also known as 90-1B5); LucPpe2m133 (also known as 133-1B2); LucPpe2m146 (also known as 146-1H2) may be employed (see U.S. Pat. No. 8,603,767, incorporated herein by reference in its entirety).

In some embodiments, assay device 100 comprises one or more labels or other scribe-able or scribed surface or surfaces on which to print, write, or display information. The label may be affixed to an outside surface by gluing, imprinting, texturing, scribing, etching, surface treating, impregnating, painting, screen printing, dyeing, coloring, embossing, or other suitable method. In some embodiments, the labels comprise directions for using the device.

In some embodiments, the assay device 100 and its component parts described herein are constructed using methods of construction known in the mechanical arts or medical device construction arts. The materials from which the assay device 100 is manufactured are varied. In some embodiments, the assay device 100 comprises a material that is metal, silicon, glass, ceramic, plastic, and synthetic and natural polymers and combinations and mixtures thereof. In some embodiments, the assay device 100 comprises a polypropylene and/or high impact polystyrene composition using an appropriate manufacturing method (e.g., pressure injection molding, machining, three-dimensional printing, etc.). In some embodiments, the assay device 100 or a component thereof is constructed using other suitable methods of manufacturing such as milling, casting, blowing, spinning, and other methods known in the mechanical arts and medical device construction.

4. KITS AND SYSTEMS

The disclosure provides kits comprising the devices or independent components thereof as disclosed herein. In some embodiments, the kits comprise: a conditionally active ATP-degrading enzyme; a swab assembly comprising: a collection swab configured to receive and absorb a sample and a cap; a reaction chamber configured to receive the swab assembly; and a reaction buffer comprising a cell lysis reagent, an inhibitor of the conditionally active ATP-degrading enzyme, an ATP detection reagent, or a combination thereof. Descriptions of the conditionally active ATP-degrading enzyme, the swab assembly, the collection swab, cap, reaction chamber, reaction buffer, inhibitors of the conditionally active ATP-degrading enzyme, and an ATP detection reagent provided elsewhere herein are suitable for use with the disclosed kits. In some embodiments, the conditionally active ATP-degrading enzyme is provided on a prewetted collection swab. In some embodiments, the reaction buffer is provided pre-loaded in a reservoir in the cap.

The reagents included in the kits may be supplied in containers of any sort such that the activity of the different components is preserved, and the components are not adsorbed or altered by the materials of the container. For example, sealed glass ampules may contain lyophilized luciferase or buffer that has been packaged under a neutral, non-reacting gas, such as nitrogen. Ampules may consist of any suitable material, such as glass, organic polymers, such as polycarbonate, polystyrene, etc., ceramic, metal or any other material typically employed to hold reagents. Other examples of suitable containers include simple bottles that may be fabricated from similar substances as ampules, and envelopes, that may consist of foil-lined interiors, such as aluminum or an alloy. Other containers include test tubes, vials, flasks, bottles, syringes, or the like. Containers may have a sterile access port such as a bottle having a stopper that may be pierced by a hypodermic injection needle. Other containers may have two compartments that are separated by a readily removable membrane that upon removal permits the components to mix. Removable membranes may be glass, plastic, rubber, etc. Individual member components of the kits may be physically packaged together or separately.

The kits can also comprise instructions for using the components of the kit. The instructions are relevant materials or methodologies pertaining to the kit. The materials may include any combination of the following: background information, list of components, brief or detailed methods for using the system, trouble-shooting, technical support, and any other related documents. Instructions can be supplied with the kit or as a separate member component, either as a paper form or an electronic form which may be supplied on computer readable memory device or downloaded from an internet website, or as recorded presentation.

The disclosure also provides systems comprising an assay device or a kit as described herein. For example, in some embodiments, the technology provides a system comprising an assay device or kit as described herein and an optical reader (e.g., luminometer) configured record, calculate, display, or communicate a result. In some embodiments, a system and/or optical reader comprises a computer-based analysis program that translates the result (e.g., the presence, absence, concentration, and/or amount of ATP) into an indicator for a user.

5. EXAMPLES

Example 1

Sample Collection and Assay Cartridge Device

To improve the sensitivity and selectivity of the live cell ATP detection cartridge design, an ATP degrading enzyme (ATPase) was incorporated in a non-lytic absorbent swab wetting solution while combining a cell lysis function within the ATP detection reagent (FIG. 1). The ATPase degrades extracellular ATP while leaving intracellular ATP intact by virtue of its sequestration inside of intact cell walls and membranes that exclude the apyrase.

The device employs a swab with an absorbent tip for collecting a sample, for example, from a potentially soiled surface by streaking the swab across that surface or from a potentially contaminated liquid applied directly to the swab.

Prior to sample collection the swab is prewetted with a solution containing a conditionally active ATP degrading enzyme (e.g., an ATPase) that substantially eliminates free ATP while leaving intracellular ATP intact. The ATPase was applied to the swab tip in a stable solution suitable for long term storage at 4° C. or for short term storage at room temperature. After sample collection and a short hold time to allow for free ATP elimination (e.g., 10-20 seconds), the swab is immersed in a cell lysis solution that also contains an inactivator of the ATPase and a luciferase-based ATP detection formulation. The lytic capacity of the formulation releases ATP from viable cells, the ATPase inhibitor protects the released ATP from the applied ATPase, and the luciferase reaction creates an ATP-dependent luminescent signal in proportion to viable cell number. Free ATP elimination by the ATPase has the effect of reducing non-cellular background ATP thereby increasing sensitivity for detecting cells and reducing the probability of false positive signals caused by free ATP.

Example 2

ATP Elimination

Figure 2:
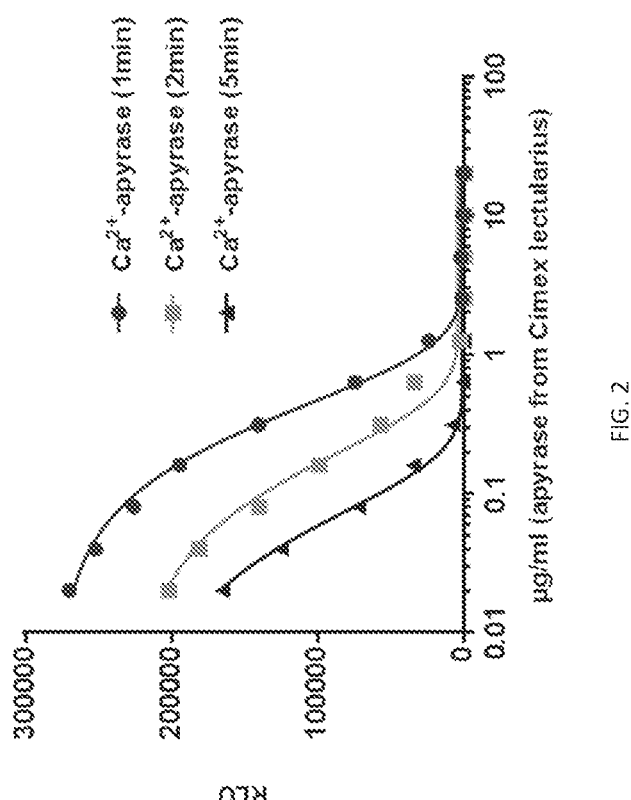
FIG. 2 is a graph of the luminescence output from $Ca^{2+}$-dependent apyrase ATP eliminators.

To test a $Ca^{2+}$-dependent apyrase for use as a conditionally active ATP eliminator, an apyrase from the bed bug *Cimex lectularius* (Cl-apyrase) was expressed as a His-tagged fusion protein in *E. coli* and purified by nickel affinity. Cl-apyrase was serially diluted to a range from 20 to 0.02 µg/ml in 25 µl of a buffer containing 50 mM Tris-HCl, pH 6.5, 50 mM NaCl, 5 mM $CaCl_2$. The diluted enzyme was dispensed into wells of a 96-well plate. 25 µl of 10 nM ATP was dispensed in all wells and incubated for 1, 2 or 5 minutes. Luciferase/luciferin detection reagent was added, and luminescent output recorded. Cl-apyrase at ~3 µg/ml eliminated all the ATP within 1 minute (FIG. 2).

In addition to the Cl-apyrase, ectonucleotide pyrophosphatase/phosphodiesterase 1 (ENPP1) was identified and tested as another enzyme that fit the criteria for use as an ATP-degrading enzyme. ENPP1 converts ATP to AMP and pyrophosphate, is zinc-dependent, and is inactivated by EGTA, by the zinc chelator N,N,N',N'-Tetrakis (2 pyridylmethyl) ethylenediamine (TPEN), and by certain small molecule inhibitors.

Figure 4:
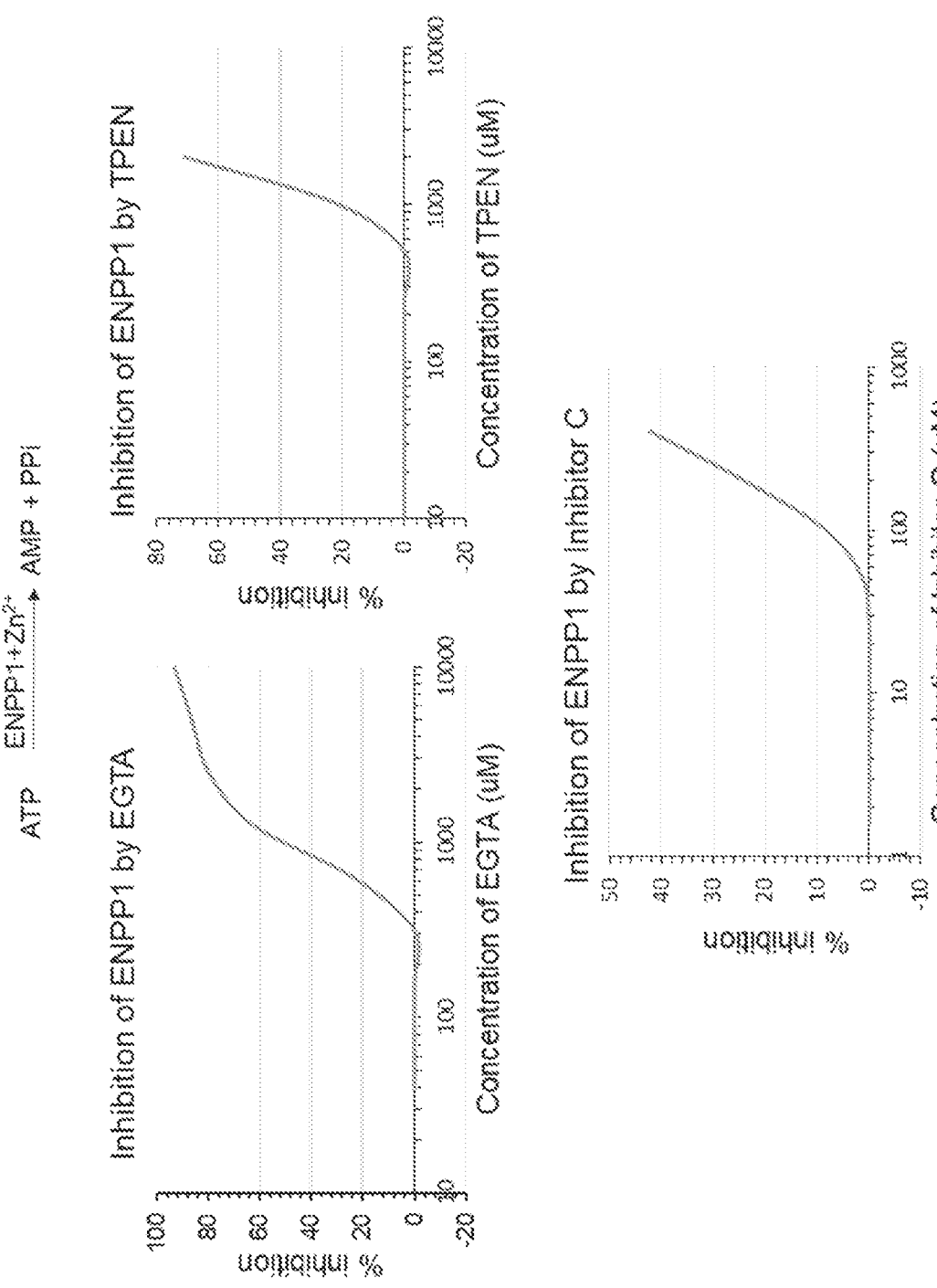
FIG. 4 is graphs of the inhibition of ENPP1 (a zinc-dependent, metal chelator sensitive ectonucleotide pyrophosphatase/phosphodiesterase) by various amounts of zinc chelators (EGTA, TPEN) or a direct small molecule ENPP1 inhibitor (Inhibitor C), as indicated.

ENPP1 (100 ng/reaction) was incubated with 10 µM ATP and varying amounts of chelators (EGTA, TPEN) or an ENPP1 selective inhibitor called inhibitor C in a reaction buffer containing 50 mM Tris HCl, pH 7.5, 250 mM NaCl, 5 uM $ZnCl_2$, 0.1 mg/ml BSA. The reactions were allowed to proceed for 60 minutes. The amount of ATP remaining was measured by the addition of a commercially available ATP detection reagent that contains luciferase and luciferin (Kinase-Glo®, Promega Corp.), as shown in FIG. 4, ENPP1 qualitatively demonstrated the conditionally active ATP eliminating properties.

Figure 3:
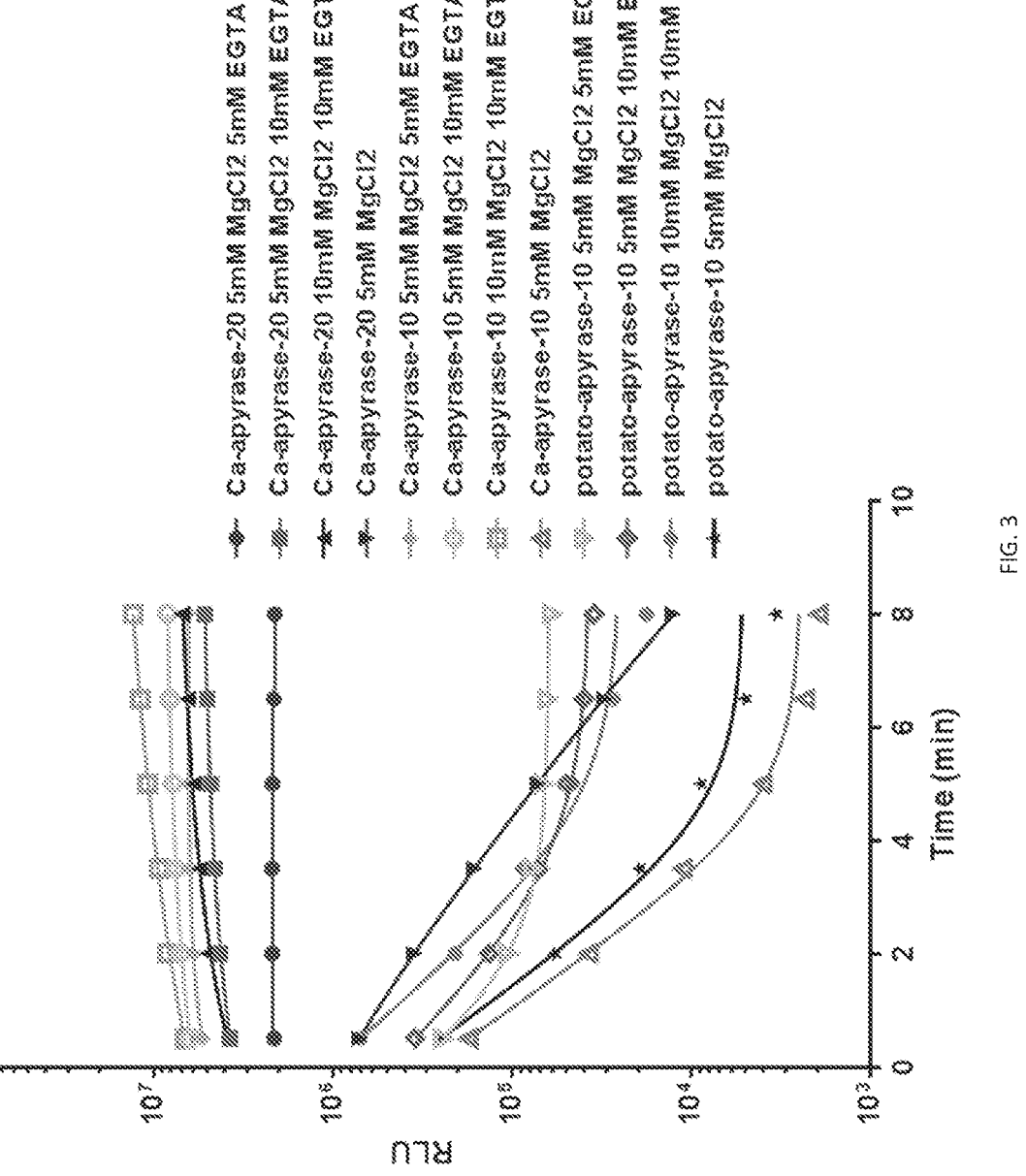
FIG. 3 is a graph of the inhibition of Ca-apyrase from *Cimex lectularius* (Cl) and $Ca^{2+}/Mg^{2+}$-apyrase from potato, *Solanum tuberosum* (St-apyrase) by EGTA.

The $Ca^{2+}/Mg^{2+}$ apyrase from potato, *Solanum tuberosum* (St-apyrase), is the most commonly used apyrase for ATP elimination. However, its inactivation requires measures, such as high temperature or extreme pH treatment, which are incompatible with the simple cartridge design disclosed here. The need for an extended heating time for apyrase inactivation is also incompatible with the goal of rapid sample collection and analysis. For comparison to Cl-apyrase (Ca-apyrase) we used a commercially available St-apyrase preparation (Sigma-Aldrich). Cl- and St-apyrase were compared for their capacity to remove extracellular ATP and to be inhibited by the $Ca^{2+}$-selective chelator EGTA. $Mg^{2+}$ is critical for luciferase activity so the $Mg^{2+}$- selective chelator EDTA was not tested. In the absence of EGTA, both enzymes eliminated ATP as indicated by a time-dependent decrease in luminescence (FIG. 3). In the presence of EGTA, St-apyrase was only partially inhibited, and thus remained substantially active (luminescence declined over time). In contrast, no Cl-apyrase activity was detected with the same amount of EGTA present (there was no decline in luminescence over time), thus demonstrating the excellent sensitivity of Cl-apyrase to inactivation by EGTA.

Example 3

*Phlebotomus papatasi* Apyrase

Figure 5A:
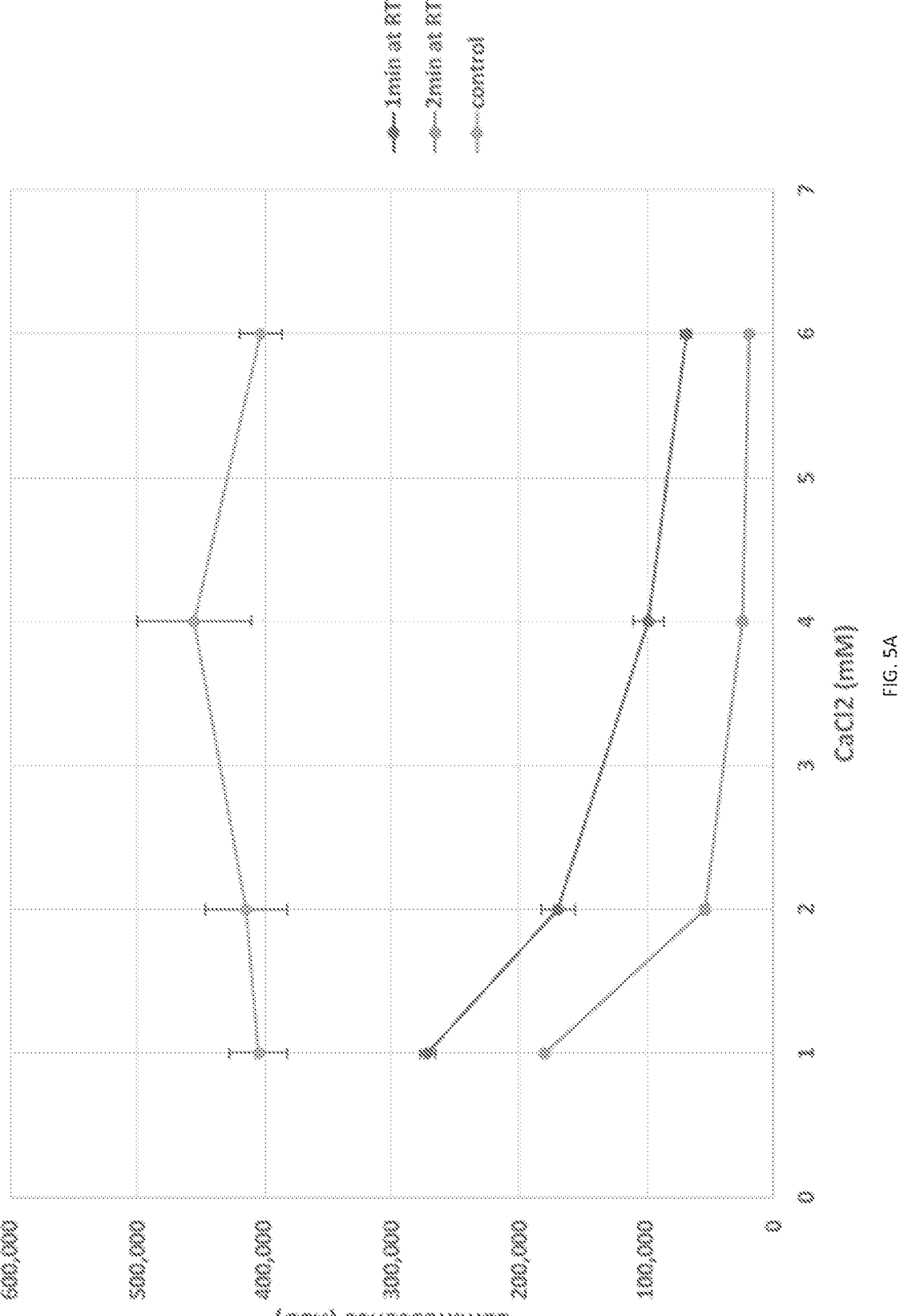
FIGS. 5A and 5B are graphs of the $Ca^{2+}$-dependence of 0.2 or 2.0 µg/100 µL sandfly *Phlebotomus papatasi* (Pp-apyrase), respectively, for degrading ATP.
Figure 5B:
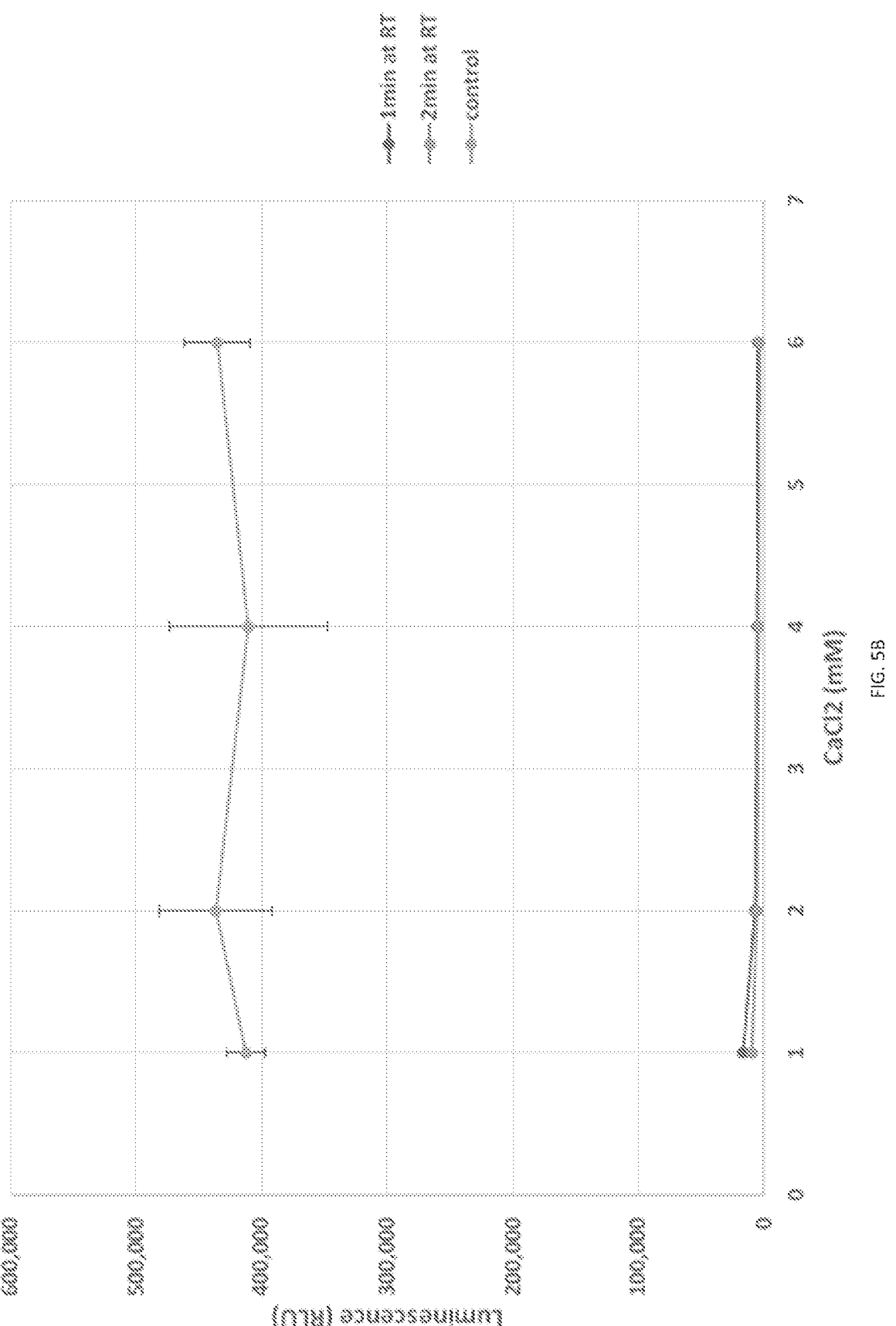

Apyrase from the sandfly *Phlebotomus papatasi* (Pp-apyrase) was also characterized for $Ca^{2+}$-dependence and sensitivity to inhibition by EGTA. Pp-apyrase was expressed as a glutathione S transferase (GST) fusion in an *E. coli* expression system and purified by glutathione affinity. The Pp-apyrase was then formulated with 100 mM HEPES pH 7.5, 0.2 mg/ml BSA, 0.1% $NaN_3$, 10% glycerol. $CaCl_2$ was included at 5 mM or in a range for 1-6 mM. FIGS. 5A and 5B show the $Ca^{2+}$-dependence of 0.2 or 2.0 mg/100 mL Pp-apyrase for degrading ATP. One- or two-minute incubations of 5 ng of ATP with Pp-apyrase were followed by addition of a commercially available ATP detection reagent (CellTiter-Glo®, Promega Corp.). Reactions were performed in microcentrifuge-style tubes and analyzed for luminescence on a single tube reading luminometer (Glo-Max® 20/20, Promega Corp.). From the reactions with 0.2 mg Pp-apyrase, it was apparent that the enzyme is most active at >4 mM $Ca^{2+}$ and 2.0 mg reactions demonstrate that nearly all the ATP can be eliminated in <1 minute.

Figure 6:
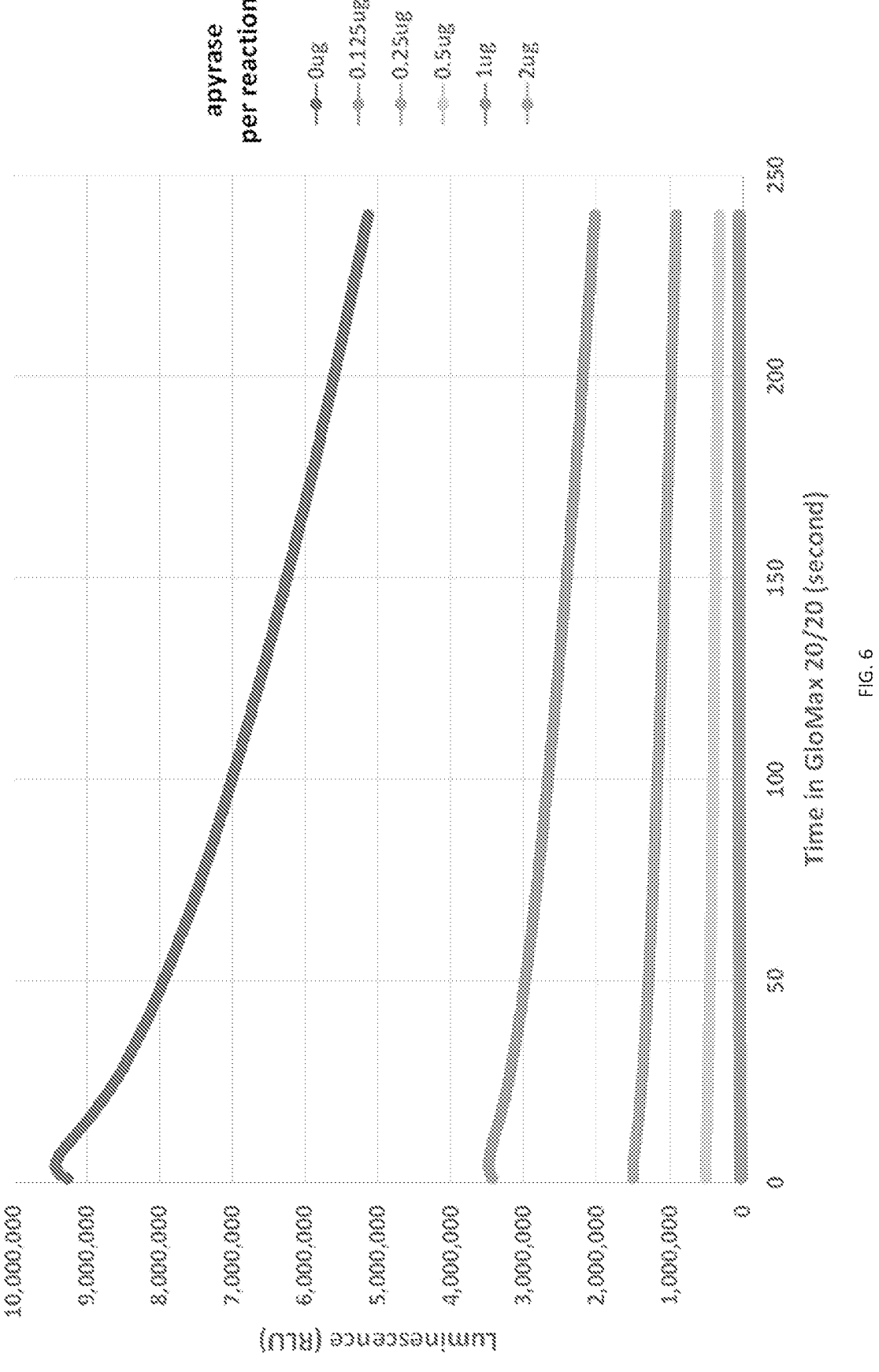
FIG. 6 is a graph of the exposure of 1 ng ATP to variable amounts of Pp-apyrase for 20 seconds followed by adding a cell lysis/ATP detection reagent.

FIG. 6 shows results from exposure of 1 ng ATP to variable amounts of Pp-apyrase for 20 seconds followed by adding a cell lysis/ATP detection reagent consisting of 100 mM HEPES pH 7.5, 10 mM $MgCl_2$, 5 mM Na Citrate, 10% glycerol, 0.2 mg/ml BSA, 10 mM EGTA, 0.02% CTAB, 0.2% Thesit, 0.002% CHEX, 200 ug/ml UltraGlo Luciferase, 3 mM D-Luciferin, and 0.1% $NaN_3$. Luminescent signals were measured over time starting immediately after addition of the lysis/ATP detection reagent. Reactions were performed in microcentrifuge-style tubes and analyzed for luminescence on a single tube reading luminometer (Glo-Max® 20/20, Promega Corp.).

Figure 7:
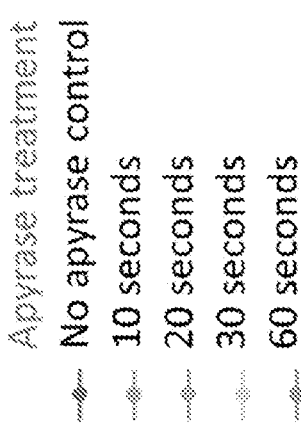
FIG. 7 is a graph of time-dependent ATP elimination by Pp-apyrase.

FIG. 7 shows time-dependent ATP elimination by Pp-apyrase, where 2 µg of the enzyme with 5 mM $Ca^{2+}$ in the formulation described for FIG. 6 eliminated all or most of a 1 ng ATP sample within 10 seconds. The legend shows incubation times with Pp-apyrase before measuring luminescence. The graph shows luminescence after the Pp-incubations when tubes are placed in the luminometer. Reactions were performed in microcentrifuge-style tubes and analyzed for luminescence on a single tube reading luminometer (GloMax® 20/20, Promega Corp.).

Figure 8:
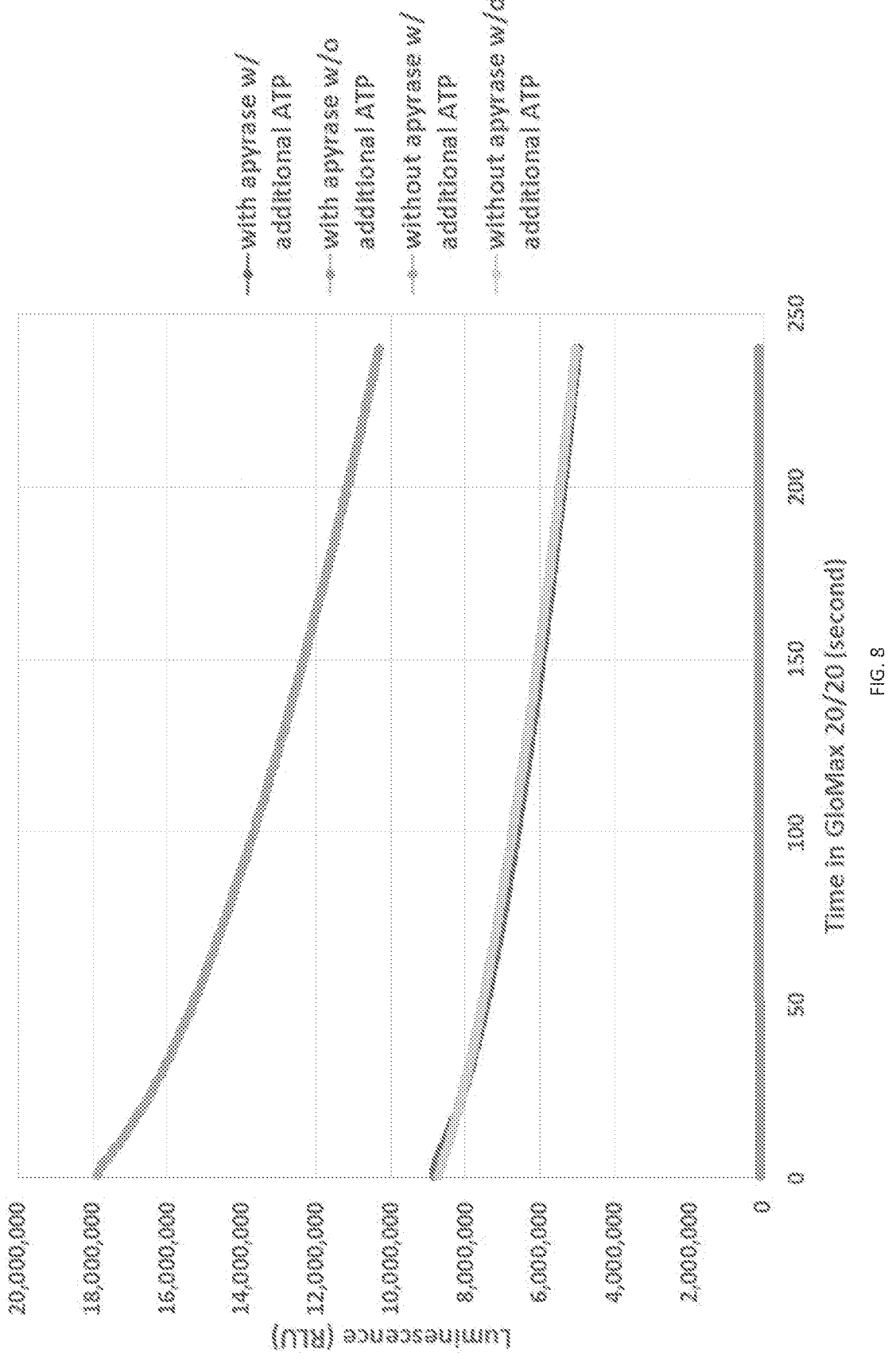
FIG. 8 is a graph similar to that in FIG. 6 in which 10 mM EGTA present in the cell lysis/ATP-detection regent inactivates Pp-apyrase.

FIG. 8 shows that the 10 mM EGTA present in the cell lysis/ATP-detection regent described for FIG. 6 effectively inactivated Pp-apyrase. This was demonstrated by showing that while the apyrase does degrade ATP before EGTA is added, it does not degrade ATP that was added after EGTA has been introduced to the mixture. Reactions were performed in microcentrifuge-style tubes and analyzed for luminescence on a single tube reading luminometer (Glo-Max® 20/20, Promega Corp.).

Thus, both calcium-dependent apyrases tested herein from the sand fly *Phlebotomus papatasi* (Pp-apyrase) and from the bed bug *Cimex lectularius* (Cl-apyrase) demonstrated a capacity for rapid and substantial ATP elimination. They were both substantially inactivated by the Ca2+-selective divalent metal chelator EGTA that was incorporated in the lysis detection reagent without substantially diminishing its lysis or ATP detection functionality. Each were also stable in a HEPES buffer formulation containing 10% glycerol, sodium azide, and bovine serum albumin and this formulation did not have a substantial effect on the lysis or ATP detection capacity of luciferase-based lysis detection reagents. Stability of the lysis detection reagent at room temperature and 4° C. allows use of a thermostable firefly luciferase enzyme (UltraGlo™ luciferase, Promega Corp.).

Example 4

Cartridge Detection

Figure 9:
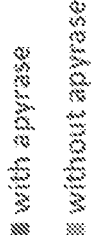
FIG. 9 is a bar graph of results from a cartridge format where ATP was applied to an absorbent swab with or without Pp-apyrase present with subsequent ATP detection.
Figure 10:
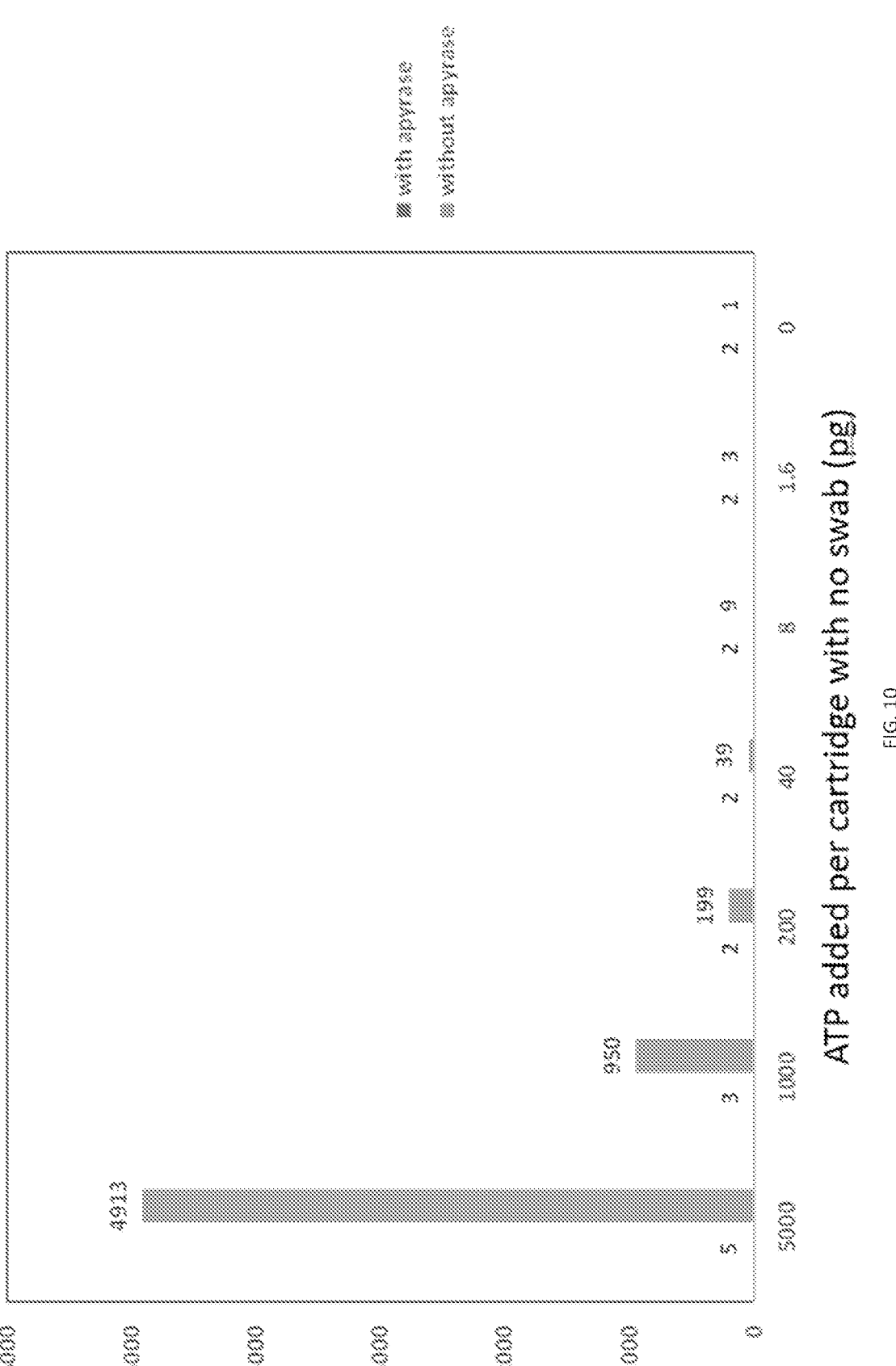
FIG. 10 is a bar graph of results from a format similar to that used in FIG. 9 but without an absorbent swab.

Apyrase from the sandfly *Phlebotomus papatasi* (Pp-apyrase) was also characterized for use in an exemplary cartridge format. The methods tested when ATP was applied to an absorbent swab with or without Pp-apyrase present with subsequent ATP detection in an exemplary cartridge (FIG. 9). Empty plastic cartridges were obtained from Empire Bio Diagnostics. Aliquots of an ATP solution were applied with a pipette to swab tips that had been prewetted with or without Pp-apyrase in the ATP Elimination Reagent formulation described above. 20 second exposures of ATP in swab tips were followed by immersion of the swab tips in the cartridge receptacle in the ATP detection/cell lysis formulation with 10 mM EGTA described for FIG. 6, and then insertion of the cartridge receptacle in a handheld luminometer (luminometer prototype by Empire Bio Diagnostics). Luminescence readings from the cartridge reflected detection of a range of ATP concentrations that were effectively eliminated by 20 second exposures to Pp-apyrase. A portion of the values shown above the vertical axis represent luminescent values too low to be visible as bars on the graph. These results are similar to those obtained in solution in microcentrifuge style tubes (See, for examples, FIGS. 6-8), demonstrating that the absorbent matrix of a swab tip does not substantially diminish apyrase activity or bioluminescent ATP detection. A similar experiment was carried out without an absorbent swab (FIG. 10) where the ATP and Pp-apyrase formulation were added directly to the cartridge receptacle. By comparison to FIG. 9, these results confirmed that the ATP elimination and detection reactions are not significantly affected by the swab matrix.

Figure 11:
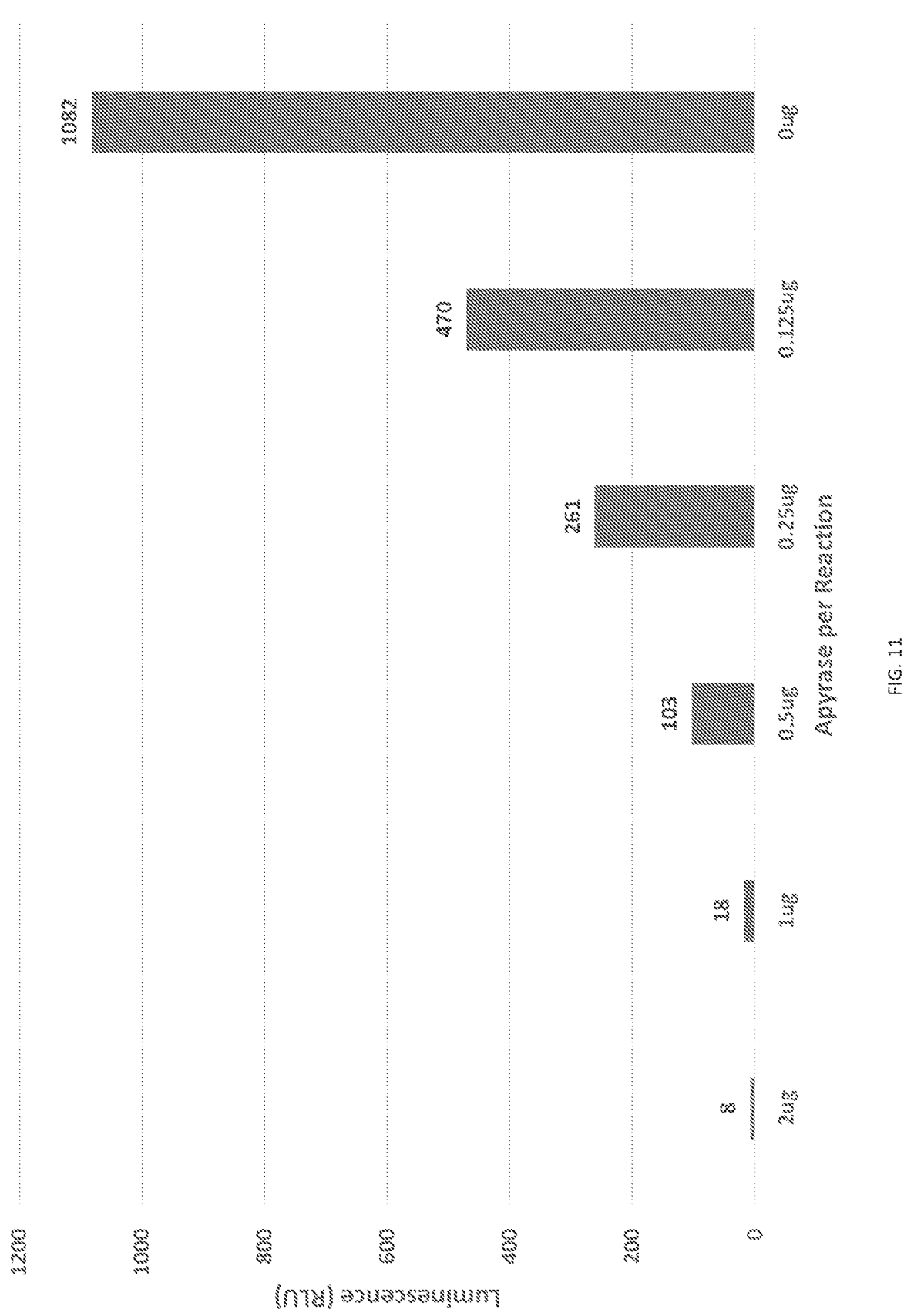
FIG. 11 is a bar graph of the dependence of ATP elimination on Pp-apyrase concentration.

The dependence of ATP elimination on Pp-apyrase concentration was investigated as shown in FIG. 11. In a 20 second reaction, 1-2 µg of the enzyme was required to eliminate most or all the ATP.

Figure 12:
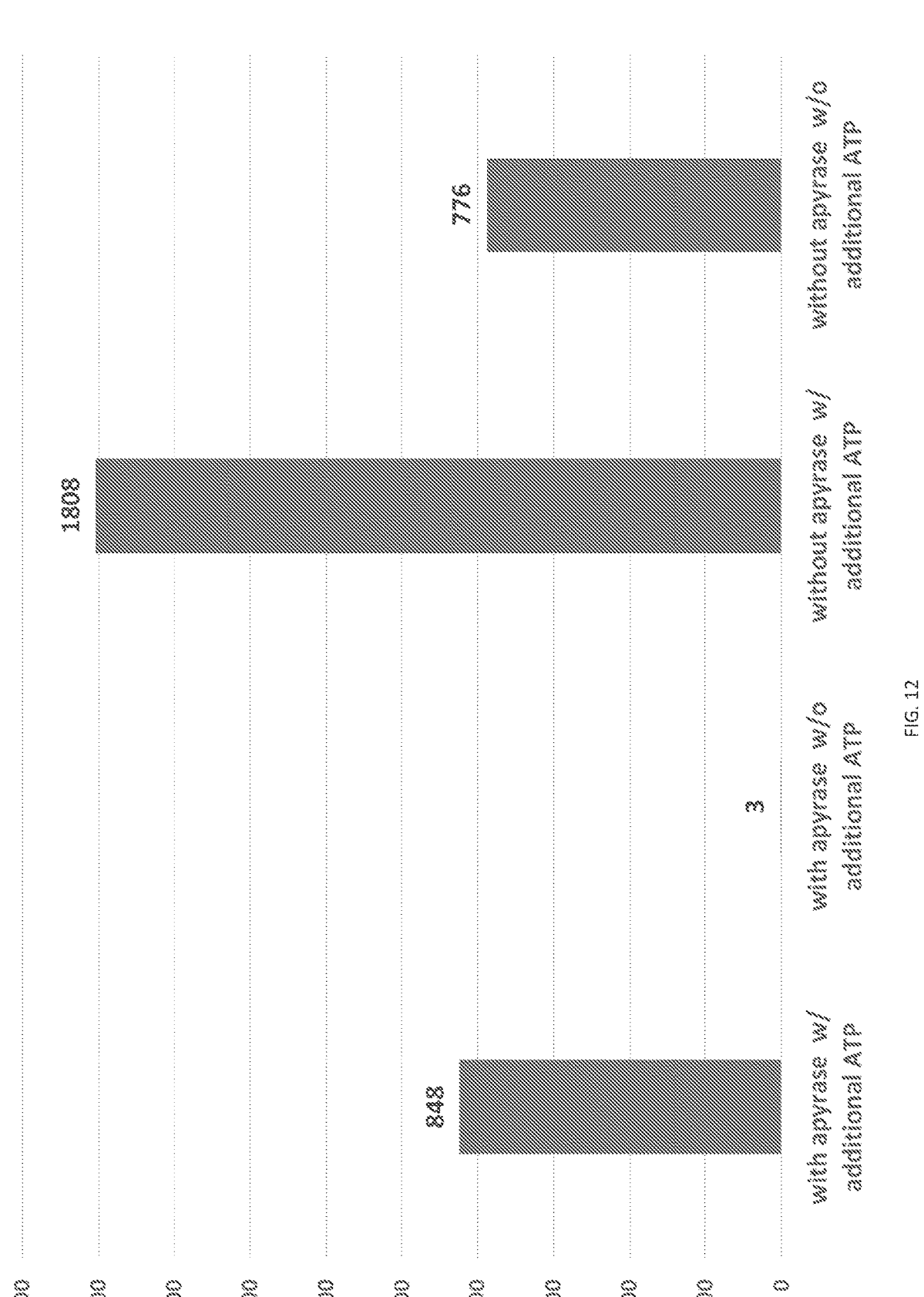
FIG. 12 is a bar graph showing effectiveness of EGTA, after an initial ATP elimination step, at inhibiting Pp-apyrase.

In the cartridge format, EGTA was effective, after an initial ATP elimination step, at inhibiting Pp-apyrase (FIG. 12). As shown in test tube format in FIG. 8, the Pp-apyrase present in the absorbent swab does not degrade ATP that is added after the lysis/ATP detection reagent with EGTA has been introduced to the mixture.

It is understood that the foregoing detailed description and accompanying examples are merely illustrative and are not to be taken as limitations upon the scope of the disclosure, which is defined solely by the appended claims and their equivalents.

Various changes and modifications to the disclosed embodiments will be apparent to those skilled in the art and may be made without departing from the spirit and scope thereof.

What is claimed is:

1. A method comprising fully or partially removing ATP contamination from a sample by incubating the sample with a conditionally active ATP-degrading enzyme selected from the group consisting of: *Cimex lectularius* apyrase, *Phlebotomus papatasi* apyrase, ectonucleotide pyrophosphatase/phosphodiesterase 1 (ENPP1), and combinations thereof.

2. The method of claim 1, wherein the sample is incubated for less than five minutes.

3. The method of claim 1, further comprising conducting a biological assay with a sample obtained following the incubating.

4. The method of claim 3, wherein the biological assay comprises detecting ATP remaining in the sample obtained following the incubating.

5. The method of claim 3, further comprising inhibiting the conditionally active ATP-degrading enzyme in a sample obtained following the incubating.

6. The method of claim 5, wherein the inhibiting comprises contacting the sample with EGTA, a zinc chelator, a small molecule inhibitor, or a combination thereof.

7. The method of claim 5, wherein the method further comprises lysing cells in a sample obtained following the incubating or prior to conducting the biological assay.

8. The method of claim 7, wherein the presence of ATP indicates presence of live cells in the sample.

9. The method of claim 4, wherein detecting the ATP remaining in the sample comprises a bioluminescent assay.

\* \* \* \* \*